United States Patent
Gérard

(10) Patent No.: US 7,241,299 B2
(45) Date of Patent: Jul. 10, 2007

(54) SURGICAL EXTRACTOR FOR EXTRACTING FOREIGN BODIES THROUGH NATURAL OR SURGICAL PASSAGES

(75) Inventor: Torchio Gérard, Verrieres le Buisson (FR)

(73) Assignee: Porges, Le Plessis Robinson (FR)

( * ) Notice: Subject to any disclaimer, the term of this patent is extended or adjusted under 35 U.S.C. 154(b) by 699 days.

(21) Appl. No.: 10/624,499

(22) Filed: Jul. 23, 2003

(65) Prior Publication Data
US 2004/0122444 A1    Jun. 24, 2004

(30) Foreign Application Priority Data
Sep. 17, 2002    (FR) ................... 02 11501

(51) Int. Cl.
*A61B 17/22* (2006.01)
(52) U.S. Cl. .................... 606/127; 606/200
(58) Field of Classification Search ............... 606/106, 606/113, 127, 128
See application file for complete search history.

(56) References Cited

U.S. PATENT DOCUMENTS

| 4,347,846 | A |   | 9/1982 | Dormia |
| 5,057,114 | A |   | 10/1991 | Wittich et al. |
| 5,484,384 | A |   | 1/1996 | Fearnot |
| 5,891,153 | A | * | 4/1999 | Peterson ............... 606/107 |
| 5,989,266 | A |   | 11/1999 | Foster |
| 6,190,394 | B1 | * | 2/2001 | Lind et al. ............ 606/127 |
| 6,224,612 | B1 |   | 5/2001 | Bates et al. |
| 6,348,056 | B1 | * | 2/2002 | Bates et al. .......... 606/114 |

FOREIGN PATENT DOCUMENTS

| WO | 9916364 | 4/1999 |
| WO | 9953849 | 10/1999 |

OTHER PUBLICATIONS

Preliminary Search Report dated May 12, 2003.

* cited by examiner

*Primary Examiner*—Michael J. Hayes
*Assistant Examiner*—Victor Nguyen
(74) *Attorney, Agent, or Firm*—Stevens, Davis, Miller & Mosher, LLP

(57) ABSTRACT

A surgical extractor for extracting foreign bodies through natural or surgical passages may include a flexible tube that penetrates inside the passages, a longitudinally rigid maneuvering wire that slides in the flexible tube and maneuvers slidably via its proximal end, and wire loops at the distal end of the maneuvering wire that may adopt a trapping position and an extracting position. The wire loops are joined at their distal ends where a tongue is formed in one of the wire loops and configured as a passage through which the other wire loops can pass with play and slide to a limited extent while maintaining squareness with respect to the wire loop having the tongue.

3 Claims, 1 Drawing Sheet

SURGICAL EXTRACTOR FOR EXTRACTING FOREIGN BODIES THROUGH NATURAL OR SURGICAL PASSAGES

FIELD OF THE INVENTION

The present invention relates to a surgical extractor for extracting foreign bodies, for example urinary calculi or gallstones, through natural or surgical passages.

BACKGROUND OF THE RELATED ART

For example, U.S. Pat. No. 4,347,846 has already disclosed a surgical extractor of this kind comprising:

a flexible tube which is able to penetrate inside said passages as far as a body to be extracted;

a longitudinally rigid maneuvering wire which is able to slide in said flexible tube and can be maneuvered slidably, from the outside, via its proximal end; and a plurality of extraction wires arranged at the distal end of said maneuvering wire and capable of adopting, under the action of the latter:

either a trapping position, for which they are arched and spaced apart from one another, forming, outside the distal end of said flexible tube, an openwork cage in the at least approximate shape of a globe, each arched wire forming a meridian thereof, or an extracting position, for which they are situated near to one another and retracted at least partially inside the distal part of said flexible tube.

In a known extractor of this kind, all of said extraction wires are made integral with one another at their distal ends by welding or similar, forming a tail protruding at the distal end of said cage.

This protruding tail has the disadvantage of preventing the distal end of the extractor from closely approaching the wall of the organ containing said foreign bodies for the purpose of trapping those situated in proximity to said wall.

Thus, in order to overcome this disadvantage, it has already been proposed (see, for example, WO 99/16364 and WO 99/53849) to omit said protruding tail by forming in one piece each pair of meridian wires situated in the same meridian plane of said cage. Thus, the latter is then formed by a plurality of independent meridian loops intersecting at the distal end of said cage.

Although such a solution indeed makes it possible to omit the distal tail mentioned above, and thus to take hold of foreign bodies near the wall of the organ containing them, it by contrast has the disadvantage that the independent meridian loops are free in relation to one another so that their relative positions and their squareness to one another can vary considerably, which leads to difficulties in grasping and/or extracting said foreign bodies.

To overcome this new disadvantage, it has therefore been proposed (see, for example, U.S. Pat. No. 5,057,114, U.S. Pat. No. 5,484,384 and U.S. Pat. No. 5,989,266) to integrate said meridian loops to one another at their distal ends, at the place where they intersect. However, doing so gives said cage a certain rigidity, preventing it from adapting to a foreign body to be extracted and to the environment in which it is situated.

SUMMARY OF THE INVENTION

The object of the present invention is to overcome this latter disadvantage and also the disadvantage resulting from the independence of said meridian loops.

To this end, according to the invention, the surgical extractor for extracting foreign bodies through natural or surgical passages, comprising:

a flexible tube which is able to penetrate inside said passages as far as such a body to be extracted;

a longitudinally rigid maneuvering wire which is able to slide in said flexible tube and can be maneuvered slidably, from the outside, via its proximal end; and a plurality of wire loops arranged at the distal end of said maneuvering wire and capable of adopting, under the action of the latter:

either a trapping position, for which said loops are deployed and form, outside the distal end of said flexible tube, an openwork cage in the at least approximate shape of a globe, each loop forming a meridian plane thereof, or an extracting position, for which said loops are flattened and retracted at least partially inside the distal part of said flexible tube, said wire loops intersecting at their distal ends by being joined to one another there, is characterized in that, at the place of their distal intersection, said wire loops are joined slidably so that each loop can slide to a limited extent relative to at least one other loop while maintaining at least approximately its squareness with respect to said other loop.

Thus, the loops of said globe are given a limited independence allowing them to adapt better to the foreign bodies to be extracted and to their environment, while not adversely affecting the extraction properties of said extractor.

At its distal end, one of said wire loops preferably comprises a passage through which the other wire loop or loops can pass with play. Such a passage can be formed between the wire of said corresponding loop and a tongue cut in the latter wire and of suitable configuration.

BRIEF DESCRIPTION OF THE DRAWINGS

From the figures in the attached drawing, it will be readily understood how the invention can be realized. In these figures, identical reference numbers designate similar elements.

DETAILED DESCRIPTION OF THE INVENTION

Figure 1:
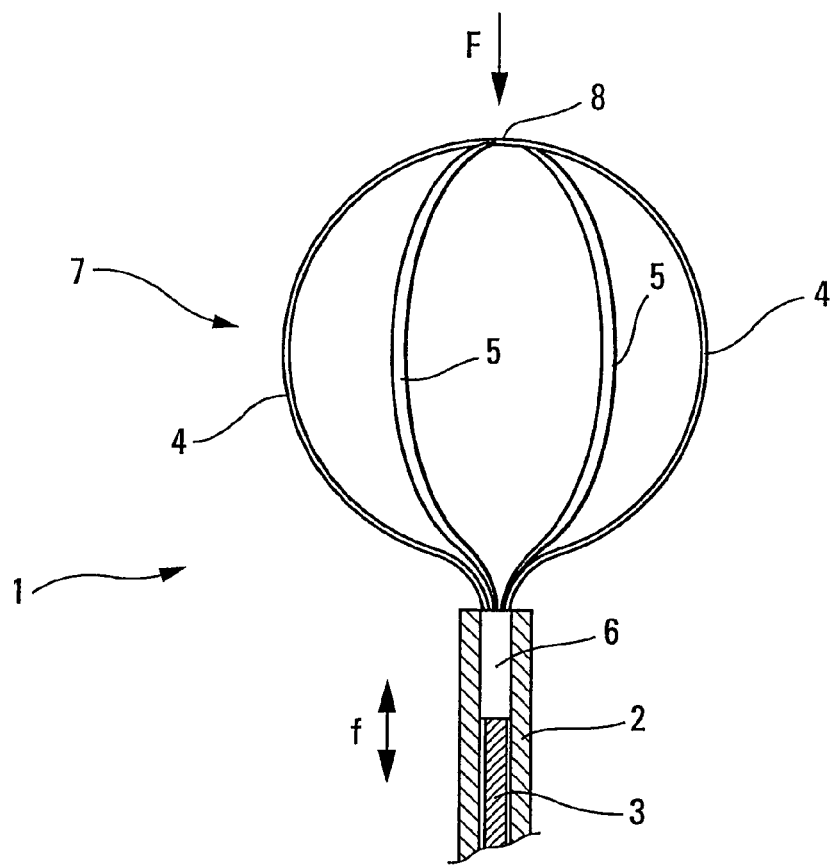
FIG. 1 is a partial and diagrammatic view of the distal part of an illustrative embodiment of the surgical extractor according to the present invention, in the deployed trapping position.

The surgical extractor 1 for extracting foreign bodies through natural or surgical passages (not shown) according to the present invention and represented in FIG. 1 comprises:

a flexible tube 2 which is able to penetrate inside said passages as far as a body to be extracted (not shown);

a longitudinally rigid maneuvering wire 3, for example formed by a cable capable of sliding in said flexible tube 2 (as illustrated by the arrow f) and to be maneuvered slidably, from the outside, via its proximal end (not shown); and two wire loops 4 and 5, for example of shape-memory alloy such as Nitinol, which are made integral at their bases with a gripper tube 6, itself integral with the distal end of the maneuvering wire 3.

Under the action of said maneuvering wire 3, the two wire loops 4 and 5 can assume:

either a deployed trapping position (represented in FIG. 1), for which the two wire loops 4 and 5 are deployed, forming, outside the distal end of the flexible tube 2, an openwork cage 7 at least approximately in the shape of a globe, said wire loops 4 and 5 forming two orthogonal meridian planes thereof;

or a withdrawn extracting position (not shown), for which the loops 4 and 5 are flattened and retracted at least partially inside the distal part of the flexible tube 2.

Figure 2:
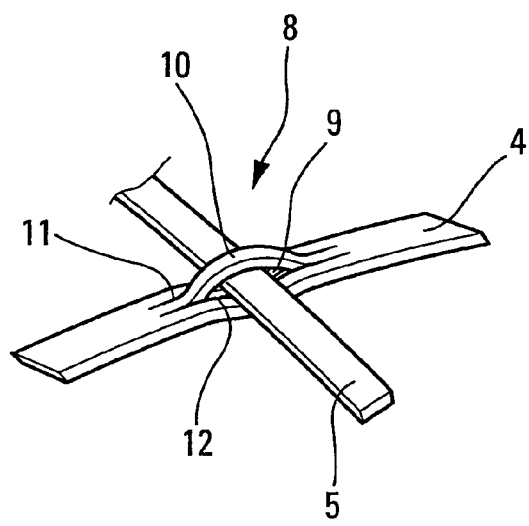
FIGS. 2 and 3 illustrate on a larger scale, and in a view according to the arrow F in FIG. 1, two alternative forms of the sliding intersection of the distal ends of the wire loops of said illustrative embodiment.
Figure 3:
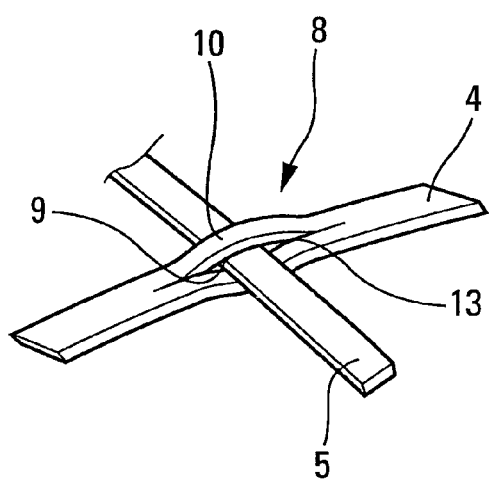

As is illustrated in FIGS. 1 through 3, at their distal ends the wire loops 4 and 5 intersect, at 8, and are joined slidably to one another so that each wire loop 4 or 5 can slide to a limited extent relative to the other wire loop 5 or 4, while maintaining at least approximately its squareness relative to the latter. To do so, as is shown in FIGS. 2 and 3, at the site of the intersection 8 the wire loop 4 comprises a passage 9 through which the wire loop 5 passes with play.

In the illustrative embodiments in FIGS. 2 and 3, said passage 9 is formed between the wire of said loop 4 and a tongue 10 cut in said wire of this loop 4 and configured in a suitable way. In FIG. 2, the tongue 10 is situated at an intermediate position in the width of the wire of the loop 4 and is delimited by two longitudinal cutting lines 11 and 12. By contrast, in FIG. 3, the tongue 10 is situated in proximity to a periphery of the wire of the loop 4 and can thus be delimited by a single longitudinal cutting line 13.

Although the illustrative embodiments described above comprise only two orthogonal loops 4 and 5, it will be readily appreciated that the surgical extractor according to the present invention can comprise at least one other additional wire loop (not shown) which, like the loop 5, would pass through the passage 9 of the loop 4, it being ensured of course that said loop 5 and said additional loop can slide with play (at angles different than 90°).

Likewise, although the cross section of the wires of the loops 4 and 5 is flat in FIGS. 1 through 3, it goes without saying that this form is not necessary and that said wires could have a round cross section.

The invention claimed is:

1. A surgical extractor for extracting foreign bodies through natural or surgical passages comprising:

a flexible tube which is able to penetrate inside said passages as far as such a body to be extracted;

a longitudinally rigid maneuvering wire which is able to slide in said flexible tube and can be maneuvered slidably, from the outside, via its proximal end; and a plurality of wire loops arranged at the distal end of said maneuvering wire and capable of adopting, under the action of the latter:

a trapping position, for which said loops are deployed and form, outside the distal end of said flexible tube, an openwork cage in the at least approximate shape of a globe, each loop forming a meridian plane thereof, and an extracting position, for which said loops are flattened and retracted at least partially inside the distal part of said flexible tube, said wire loops intersecting at their distal ends and being joined to one another there, wherein, at the place of the distal intersection of said wire loops, said surgical extractor comprises a tongue formed in the wire of one of said wire loops and configured in a passage through which each other wire loop can pass with play and slide to a limited extent while maintaining at least approximately its squareness with respect to said wire loop having said tongue.

2. The surgical extractor of claim 1, wherein said tongue is situated at an intermediate position in the width of said wire and is delimited by two longitudinal cutting lines.

3. The surgical extractor of claim 1, wherein said tongue is situated in proximity to a periphery of said wire and is delimited by said periphery and a single longitudinal cutting line.

* * * * *